United States Patent
Narayanaswamy et al.

(10) Patent No.: US 10,828,003 B2
(45) Date of Patent: Nov. 10, 2020

(54) SYSTEM AND METHOD FOR MITIGATING ELECTROMAGNETIC INTERFERENCE WHEN ACQUIRING IMAGE DATA

(71) Applicant: GE Precision Healthcare, LLC, Wauwatosa, WI (US)

(72) Inventors: Mahesh Raman Narayanaswamy, Milwaukee, WI (US); Catherine Noel Bailey, Waukesha, WI (US); Joseph John Kulak, Milwaukee, WI (US); Jeffrey Alan Kautzer, Pewaukee, WI (US); Douglas Albagli, Clifton Park, NY (US); Jeffrey Lange, Pewaukee, WI (US)

(73) Assignee: GE Precision Healthcare, LLC, Wauwatosa, WI (US)

( * ) Notice: Subject to any disclaimer, the term of this patent is extended or adjusted under 35 U.S.C. 154(b) by 4 days.

(21) Appl. No.: 16/356,485

(22) Filed: Mar. 18, 2019

(65) Prior Publication Data

US 2020/0297302 A1    Sep. 24, 2020

(51) Int. Cl.
*A61B 6/03*    (2006.01)
*A61B 6/00*    (2006.01)
*G06T 5/00*    (2006.01)
*G06T 5/50*    (2006.01)

(52) U.S. Cl.
CPC .............. *A61B 6/5258* (2013.01); *A61B 6/54* (2013.01); *G06T 5/002* (2013.01); *G06T 5/50* (2013.01); *G06T 2207/10116* (2013.01)

(58) Field of Classification Search
None
See application file for complete search history.

(56) References Cited

U.S. PATENT DOCUMENTS

| | | | |
|---|---|---|---|
| 7,408,168 B1 | 8/2008 | Aufrichtig | |
| 7,495,228 B1 | 2/2009 | Albagli et al. | |
| 7,649,979 B2* | 1/2010 | Liu | H04N 5/32 378/207 |
| 7,679,062 B2* | 3/2010 | Hawver | G01T 7/00 250/370.14 |
| 8,384,041 B2* | 2/2013 | Tredwell | H01L 27/14663 250/370.09 |
| 8,693,747 B2* | 4/2014 | Xue | A61B 6/4233 250/370.09 |
| 2009/0251125 A1* | 10/2009 | Hawver | G01T 7/00 323/355 |
| 2009/0290686 A1 | 11/2009 | Liu et al. | |
| 2012/0018627 A1* | 1/2012 | Tredwell | H04N 5/361 250/252.1 |
| 2012/0275569 A1* | 11/2012 | Xue | A61B 6/4233 378/91 |

OTHER PUBLICATIONS

European application 20163193.4 filed Mar. 13, 2020-Search Report dated Jun. 4, 2020, 8 pages.

* cited by examiner

*Primary Examiner* — Thomas R Artman

(57) ABSTRACT

A digital X-ray detector is provided. The digital X-ray detector includes control circuitry. The control circuitry is configured to obtain an electromagnetic interference (EMI) frequency of an EMI signal, to receive a signal to start a scan, to ensure EMI noise is in a same phase during acquisition of offset images and read images to enable a subtraction of the EMI noise, and to start the scan.

16 Claims, 8 Drawing Sheets

SYSTEM AND METHOD FOR MITIGATING ELECTROMAGNETIC INTERFERENCE WHEN ACQUIRING IMAGE DATA

BACKGROUND

The subject matter disclosed herein relates generally to digital X-ray imaging systems and, more particularly, to techniques for mitigating the effects of electromagnetic interference (EMI) during image acquisition with such systems.

A number of radiological and fluoroscopic imaging systems of various designs are known and are presently in use. Such systems generally are based upon generation of X-rays that are directed toward a subject of interest. The X-rays traverse the subject and impact a digital detector or an image intensifier. In medical contexts, for example, such systems may be used to visualize internal bones, tissues, and organs, and diagnose and treat patient ailments. In other contexts, parts, baggage, parcels, and other subjects may be imaged to assess their contents. In addition, radiological and fluoroscopic imaging systems may be used to identify the structural integrity of objects and for other purposes.

Increasingly, such X-ray systems use digital circuitry, such as solid-state detectors, for detecting the X-rays, which are attenuated, scattered or absorbed by the intervening structures of the subject. It will be appreciated that raw image data acquired via such X-ray systems may include a number of artifacts or other undesirable elements that may, if left uncorrected, result in visual artifacts in a reconstructed image based on the raw image data. In turn, these visual artifacts may negatively impact the ability of a user or computer to discern finer details in the image. Some artifacts may be due to presence of electromagnetic interference (EMI) in the imaging environment. Sources of EMI may include, for example, various electrical and electronic components that may be utilized in the vicinity of the X-ray imaging system. There is a need, therefore, for improved approaches to mitigate the effects of EMI during image acquisition.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with an embodiment, a digital X-ray detector is provided. The digital X-ray detector includes control circuitry. The control circuitry is configured to obtain an electromagnetic interference (EMI) frequency of an EMI signal, to receive a signal to start a scan, to ensure EMI noise is in a same phase during acquisition of offset images and read images to enable a subtraction of the EMI noise, and to start the scan.

In accordance with another embodiment, an X-ray imaging method is provided. The method includes utilizing a digital X-ray detector to obtain an electromagnetic interference (EMI) frequency of an EMI signal, to receive a signal to start a scan, to ensure EMI noise is in a same phase during acquisition of offset images and read images to enable a subtraction of the EMI noise, and to start the scan.

In accordance with a further embodiment, an imaging system is provided. The imaging system includes an X-ray source and a digital X-ray detector. The imaging system also includes control circuitry configured, via the digital X-ray detector, to obtain an electromagnetic interference (EMI) frequency of an EMI signal, to receive a signal to start a scan, to ensure EMI noise is in a same phase during acquisition of offset images and read images to enable a subtraction of the EMI noise, and to start the scan.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present disclosure provides for methods and systems to synchronize X-ray image acquisition sequences for radiographic detectors where time dependent noise (e.g., row correlated noise which occurs in a direction of the sampling) is present due to electromagnetic interference (EMI) such as low frequency EMI (e.g., 60 Hertz (Hz) or less). The techniques discussed below may synchronize the scans of the detector to occur at a particular time period that is a multiple of a period of the EMI signal. The scans may include a read or readout (where the detector panel is scanned and detector data such as X-ray image data is acquired) or a scrub (where the detector panel is scanned to reset the detector circuitry but no data is read). In certain embodiments, the EMI frequency may be determined from offset data or dark images (i.e., detector data collected in the absence of radiation). The offset data may be utilized to correct the X-ray image data to generate corrected X-ray images where EMI artifacts are minimized due to the cancellation of the time dependent noise. The EMI mitigation techniques may be utilized across all orientations (X-, Y-, and Z-axes). The techniques described below may be utilized in a variety of radiographic imaging systems, such as computed tomography (CT) systems, fluoroscopic imaging systems, mammography systems, tomosynthesis imaging systems, conventional radiographic imaging systems, and so forth. However, it should be appreciated that the described techniques may also be used in non-medical contexts (such as security and screening systems and non-destructive detection systems).

Figure 1:
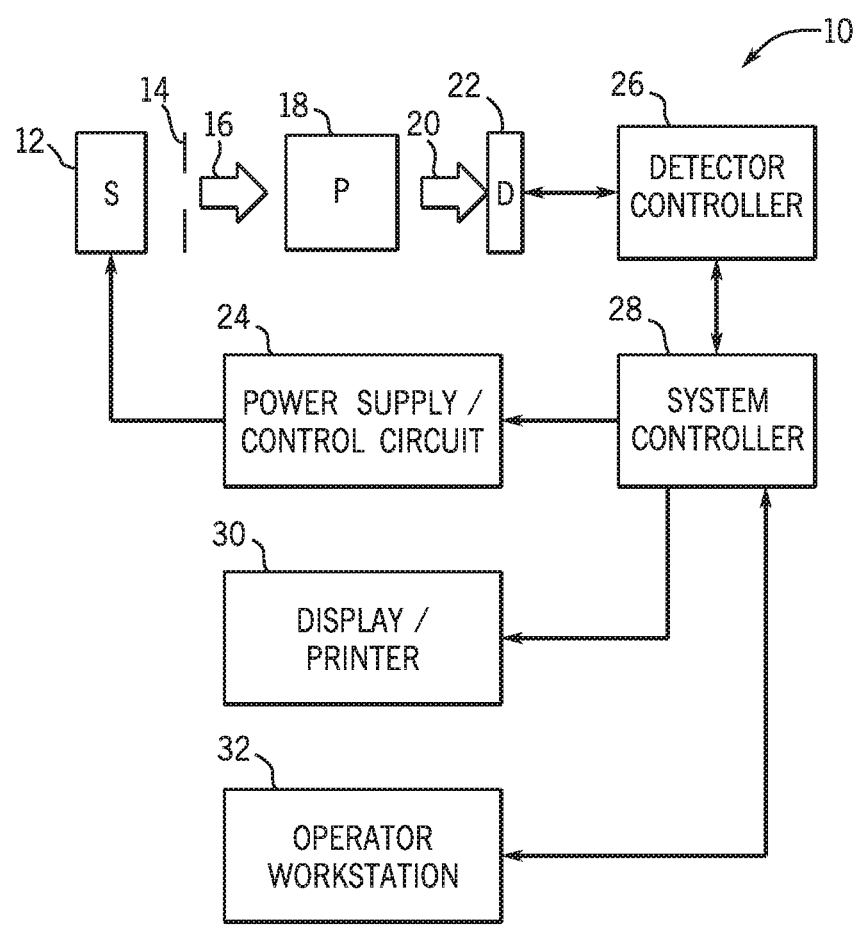
FIG. 1 is a diagrammatical overview of a digital X-ray imaging system in which the present technique may be utilized.

Turning now to the drawings, FIG. 1 illustrates diagrammatically an imaging system 10 for acquiring and processing discrete pixel image data. In the illustrated embodiment, system 10 is a digital X-ray system designed both to acquire original image data and to process the image data for display in accordance with the present technique. The imaging system 10 may be a stationary system disposed in a fixed X-ray imaging room or a mobile X-ray system. In the embodiment illustrated in FIG. 1, imaging system 10 includes a source of X-ray radiation 12 positioned adjacent to a collimator 14. Collimator 14 permits a stream of radiation 16 to pass into a region in which a subject, such as a human patient 18 is positioned. A portion of the radiation 20 passes through or around the subject and impacts a digital X-ray detector, represented generally at reference numeral 22. The detector 22 may be portable or permanently mounted to the system 10. In certain embodiments, the detector 22 may convert the X-ray photons incident on its surface to lower energy photons, and subsequently to electric signals, which are acquired and processed to reconstruct an image of the features within the subject. In other embodiments, such as in a direct conversion implementation, the incident radiation itself may be measured without an intermediary conversion process.

Source 12 is controlled by a power supply/control circuit 24 which furnishes both power and control signals for examination sequences. Moreover, detector 22 is coupled to a detector controller 26 which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data. In the present context, system controller 28 also includes signal processing circuitry, typically based upon a general purpose or application-specific digital computer; and associated manufactures, such as optical memory devices, magnetic memory devices, or solid-state memory devices, for storing programs and routines executed by a processor of the computer to carry out various functionalities (e.g., offset correction to remove EMI generate artifacts), as well as for storing configuration parameters and image data; interface protocols; and so forth. In one embodiment, a general or special purpose computer system may be provided with hardware, circuitry, firmware, and/or software for performing the functions attributed to one or more of the power supply/control circuit 24, the detector controller 26, and/or the system controller 28 as discussed herein.

In the embodiment illustrated in FIG. 1, system controller 28 is linked to at least one output device, such as a display or printer as indicated at reference numeral 30. The output device may include standard or special purpose computer monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
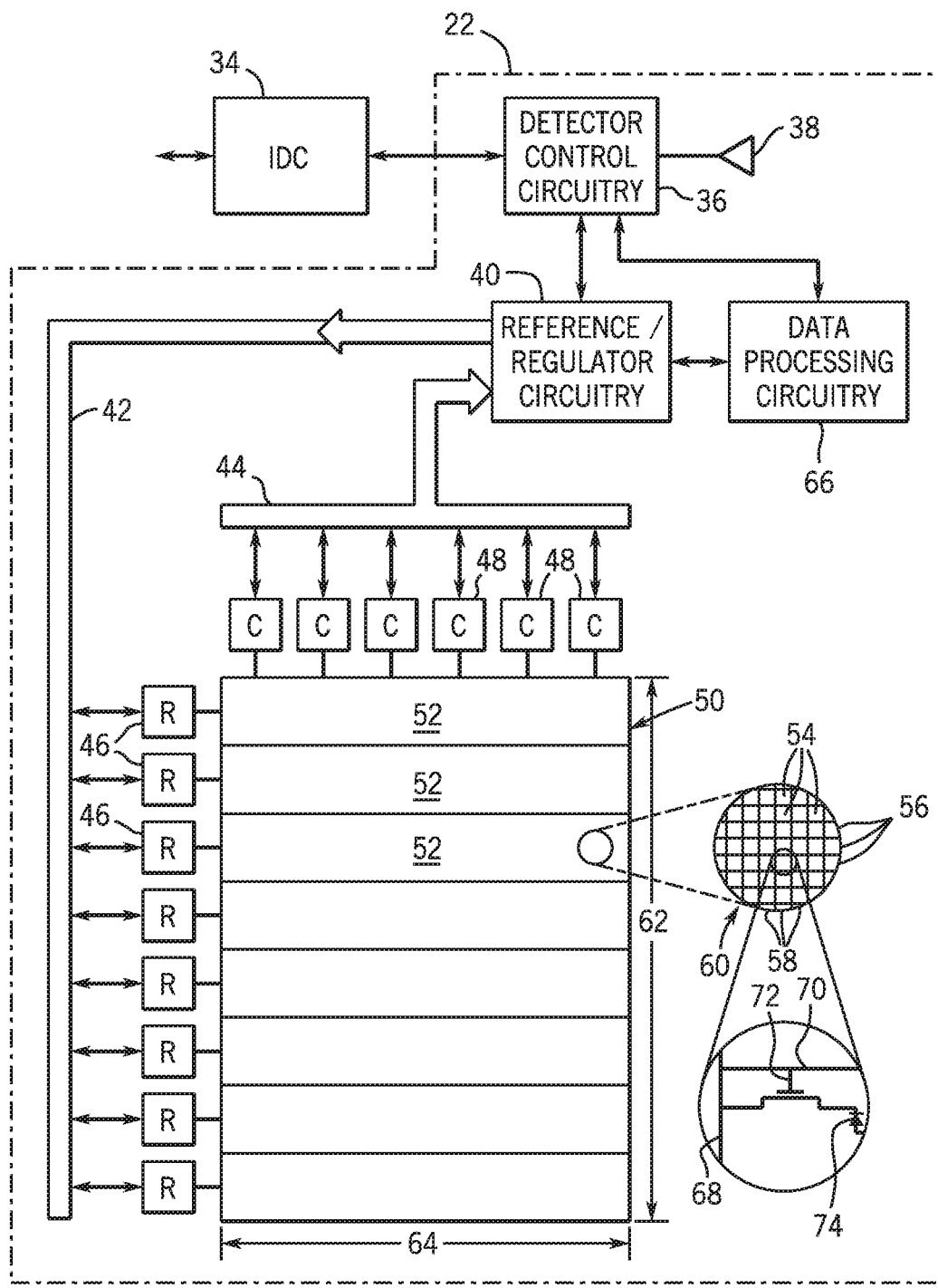
FIG. 2 is a diagrammatical representation of the functional circuitry in a detector of the system of FIG. 1 to produce image data for reconstruction.

FIG. 2 is a diagrammatical representation of functional components of digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. In one implementation, IDC 34 is coupled via two-way fiberoptic conductors to detector control circuitry 36 within detector 22. In certain presently contemplated embodiments, other communications systems and technologies may be used, such as Ethernet communications protocols, and wireless communications devices and protocols. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column electronics used to acquire image data during data acquisition phases of operation of the system. Circuitry 36 therefore transmits power and control signals to reference/regulator circuitry 40, and receives digital image pixel data from circuitry 40.

In a present embodiment, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions of the detector surface. In certain presently contemplated embodiments, the X-ray photons may be directly converted to electrical signals. Readout electronics convert the resulting analog signals to digital values that can be processed, stored, and displayed, such as in a display 30 or a workstation 32 following reconstruction of the image. In a present form, the array of photodetectors is formed of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and the electrode of each column is connected to an individual data channel of the readout electronics.

In the particular embodiment illustrated in FIG. 2, by way of example, a row bus 42 includes a plurality of conductors for enabling readout from various rows of the detector 22, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50, which may be subdivided into a plurality of sections 52. Each section 52 is coupled to one of the row drivers 46, and includes a number of rows. Similarly, each column driver 48 is coupled to a series of columns. The photodiode and transistor arrangement mentioned above thereby define a series of pixels or discrete picture elements 54 which are arranged in rows 56 and columns 58. The rows and columns define an image matrix 60, having a height 62 and a width 64.

As also illustrated in FIG. 2, each pixel 54 is generally defined at a row and column crossing, at which a column electrode (or data line) 68 crosses a row electrode (or scan line) 70. As mentioned above, a thin film transistor 72 is provided at each crossing location for each pixel, as is a photodiode 74. As each row is enabled by row drivers 46, signals from each photodiode 74 may be accessed via readout electronics 48, and converted to digital signals for subsequent processing and image reconstruction. Thus, an entire row of pixels in the array is controlled simultaneously when the scan line 70 attached to the gates of all the transistors of pixels on that row is activated. Consequently, each of the pixels in that particular row is connected to a data line 68, through a switch, which is used by the readout electronics to restore the charge to the photodiode 74 and measure an amount of charge depletion resulting from irradiation.

It should be noted that in certain systems, as the charge is restored to all the pixels in a row simultaneously by each of the associated dedicated readout channels, the readout electronics is converting the measurements from the previous row from an analog voltage to a digital value. Furthermore, the readout electronics may transfer the digital values from rows previous to the acquisition subsystem, which will perform some processing prior to displaying a diagnostic image on a monitor or writing it to film. In at least some embodiments, the digital detector 22 may include data processing circuitry 66 configured to perform some local processing of the data acquired via the detector panel 50 within the digital detector itself. For instance, as discussed in greater detail below, the digital detector 22 may be configured to perform synchronization of scans (e.g., scrub and/or read) as a multiple of a period of an EMI signal and offset correction (e.g., to reduce EMI generated noise such as row correlated noise) to the acquired data independent of a host processing system, such as the system controller 28. Additionally, in one embodiment, the digital detector 22 apply such correction to the acquired data before outputting the data to other components of the system 10.

The circuitry used to enable the rows may be referred to in a present context as row enable or field effect transistor (FET) circuitry based upon the use of field effect transistors for such enablement (row driving). The FETs associated with the row enable circuitry described above are placed in an "on" or conducting state for enabling the rows, and are turned "off" or placed in a non-conducting state when the rows are not enabled for readout. Despite such language, it should be noted that the particular circuit components used for the row drivers and column readout electronics may vary, and the present invention is not limited to the use of FETs or any particular circuit components.

Figure 3:
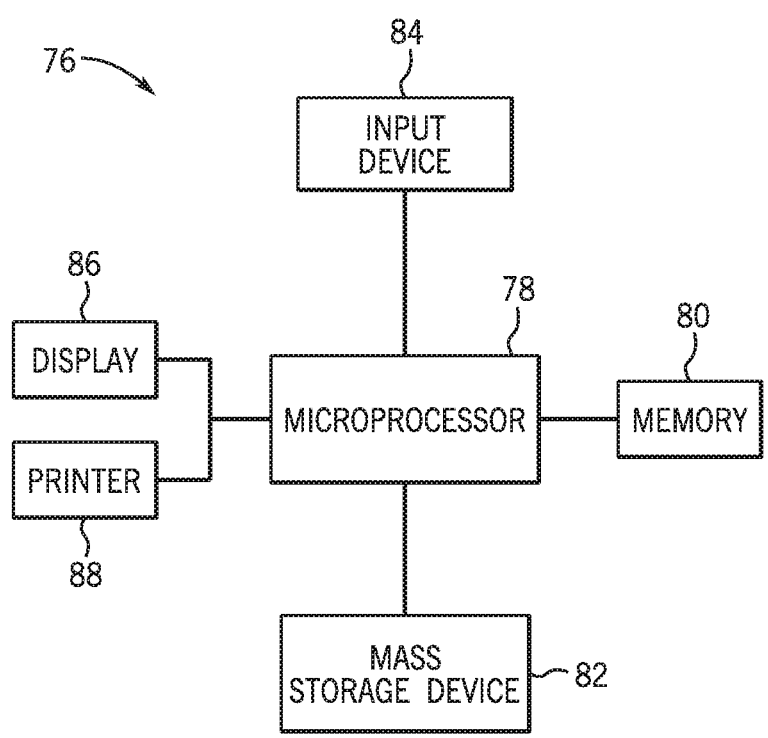
FIG. 3 is a block diagram of a processor-based device or system that may be configured to implement functionality described herein in accordance with one embodiment.

Various functionality, including image data correction described herein, may be performed by, or in conjunction with, a processor-based system 76, which is generally depicted in FIG. 3 in accordance with one embodiment. For example, the various controllers and circuitry discussed herein may include, or be partially or entirely embodied in, a processor-based system, such as that presently illustrated. The processor-based system 76 may be a general-purpose computer, such as a personal computer, configured to run a variety of software, including software implementing all or part of the functionality described herein. Alternatively, in other embodiments, the processor-based system 76 may include, among other things, a distributed computing system, or an application-specific computer or workstation configured to implement all or part of the presently described functionality based on specialized software and/or hardware provided as part of the system. Further, the processor-based system 76 may include either a single processor or a plurality of processors to facilitate implementation of the presently disclosed functionality.

In one embodiment, the exemplary processor-based system 76 includes a microcontroller or microprocessor 78, such as a central processing unit (CPU), which executes various routines and processing functions of the system 76. For example, the microprocessor 78 may execute various operating system instructions, as well as software routines configured to effect certain processes, stored in or provided by a manufacture including one or more computer readable-media (at least collectively storing the software routines), such as a memory 80 (e.g., a random access memory (RAM) of a personal computer) or one or more mass storage devices 82 (e.g., an internal or external hard drive, a solid-state storage device, or another storage device). In addition, the microprocessor 78 processes data provided as inputs for various routines or software programs, such as data provided as part of the present subject matter described herein in computer-based implementations.

Such data may be stored in, or provided by, the memory 80 or mass storage device 82. Alternatively, such data may be provided to the microprocessor 78 via one or more input devices 84. The input devices 84 may include manual input devices, such as a keyboard, a mouse, or the like. In addition, the input devices 84 may include a network device, such as a wired or wireless Ethernet card, a wireless network adapter, or any of various ports or devices configured to facilitate communication with other devices via any suitable communications network, such as a local area network or the Internet. Through such a network device, the system 76 may exchange data and communicate with other networked electronic systems, whether proximate to or remote from the system 76.

Results generated by the microprocessor 78, such as the results obtained by processing data in accordance with one or more stored routines, may be provided to an operator via one or more output devices, such as a display 86 and/or a printer 88. Based on the displayed or printed output, an operator may request additional or alternative processing or provide additional or alternative data, such as via the input device 84. Communication between the various components of the processor-based system 76 may typically be accomplished via a chipset and one or more busses or interconnects which electrically connect the components of the system 76. In one embodiment, the exemplary processor-based system 76 can be configured to, among other things, receive image data, receive offset data, apply offset correction to the image data via the offset data, and output the corrected image data.

Figure 4:
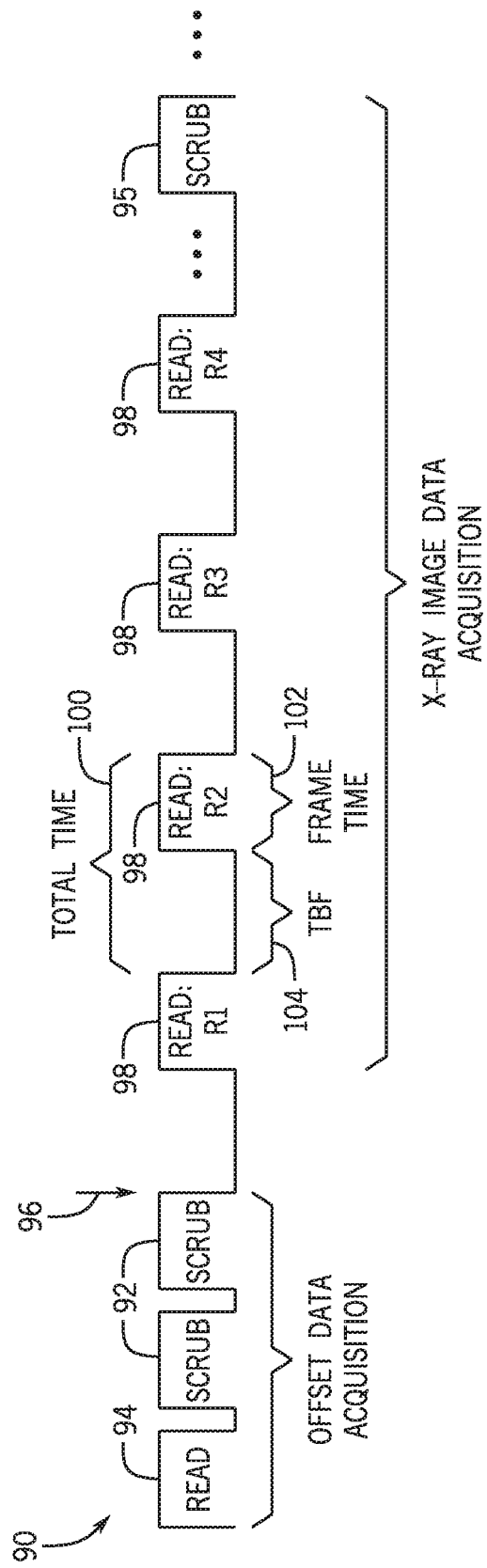
FIG. 4 is a diagrammatical representation of a portion of an acquisition sequence in which both image data and offset data are acquired for correction of electromagnetic interference (EMI) artifacts.

FIG. 4 represents an image data acquisition protocol timeline designed to permit the correction of image data for EMI artifacts in accordance with the techniques discussed below. The timeline, designated generally by reference numeral 90 may include periods of the detector performing various scans for scrubbing and data readout operations. As will be appreciated by those skilled in the art, to account for inevitable loss of charge of the photodiodes of the detector, it may be useful to recharge the photodiodes periodically by a scrubbing operation as indicated by frame 94 prior to activation of the X-ray source and frame 95 subsequent to activation of the X-ray source. Essentially, such operations stabilize the FET threshold voltage but do not readout data. Prior to the X-ray source being activated, readout (as indicated by frame 94) of the detector enables the acquisition of offset images or dark images (i.e., images acquired when the detector is not exposed to radiation from the source). As depicted, only a single readout is depicted prior to activation of the X-ray source. In certain embodiments, a plurality of offset images (e.g., 2, 3, 4, etc.) may be acquired prior to activation of the X-ray source. The offset data that is read out may also be similarly affected by the EMI, when such EMI is present. As described in greater detail below, a respective frequency (e.g., 50 Hz, 60 Hz, etc.) of one or more EMI signals may be determined from one or more offset images. At some point in the data acquisition protocol, the X-ray source will be activated (e.g., as indicated by arrow 96) such that the detector is impacted by X-ray radiation during a reception period. The X-ray radiation will cause depletion in the charge of the photodetectors at each pixel location corresponding to the amount of X-ray radiation received at the location on the scintillator. The X-ray reception period is followed by one or more data readouts as indicated by frames 98. These readouts 98, may also include readout of X-ray image data that is affected by EMI, when EMI is present at the system. As described in greater detail below, the frequency of the EMI may be utilized in synchronizing the scans (e.g., X-ray image scans 98, scrubs 92) that occur subsequent to the activation of the X-ray source. In particular, these scans may be synchronized to a master clock in the detector hardware (e.g., FPGA) so that each scan is started at a multiple of a period (i.e., amount of time to complete a single cycle) of the EMI signal. In certain embodiments, when multiple low frequency (e.g. 60 Hz or less) EMI signals are present, the scans may be synchronized so that each scan is started at a multiple of the each respective period of the multiple EMI signals. Row correlated noise (e.g., due to the EMI) is minimized when a total time 100 from the end of one scan or frame to the end of the next scan or frame time is synchronized with the frequency of the EMI. The total time 100 equals the frame time 102 (e.g., duration of scan) and a time between frames (TBF) or scans 104. The one or more offset images acquired above may be utilized in correcting X-ray image data during the synchronized scans to remove EMI artifacts.

Figure 5:
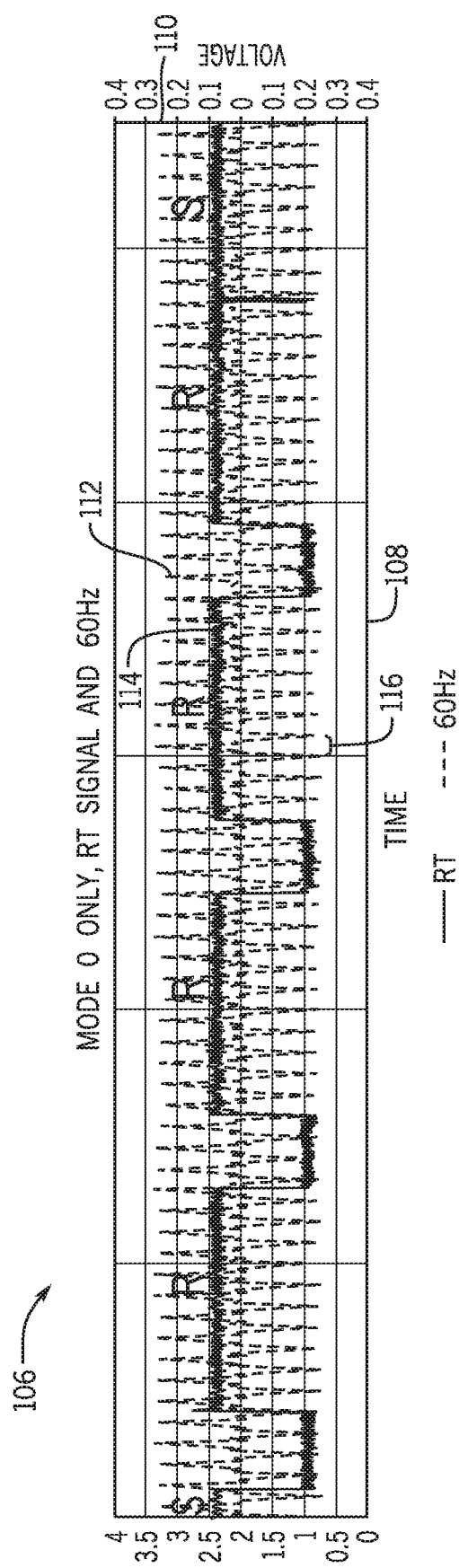
FIG. 5 is a graphical representation of a low frequency magnetic field overlaid on a detector signal.

FIG. 5 is a graphical representation 106 (e.g., from an oscilloscope) of a low frequency magnetic field overlaid on a detector signal. The graph 106 includes an X-axis 108 representing time and a Y-axis 110 representing voltage. As depicted, a signal 112 of low frequency magnetic field (e.g., 60 Hz) is overlaid on a detector signal 114. The detector signal 114 includes scrub (S) and readout (R) periods. As depicted, the magnetic field signature goes through numerous periods 116, a scrub or readout period. As described in greater detail below, synchronization of the scrubs (i.e., scrubs and/or readouts) to a multiple of the period of the signal 112 may be utilized to minimize EMI artifacts in the generated X-ray images.

Figure 6:
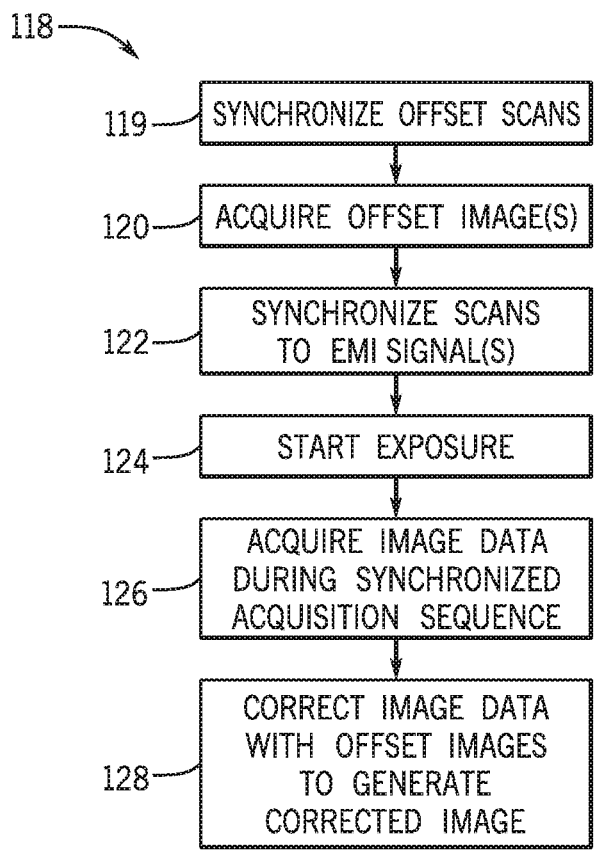
FIG. 6 is a flow chart of an embodiment of a method for correcting EMI artifacts in image data.

FIG. 6 is a flow chart of an embodiment of a method 118 for correcting EMI artifacts in image data. One or more of the steps may be performed by control/processing circuitry of the digital X-ray detector 22, another component of the imaging system 10 (e.g., system controller 28), or a remote processing device. The method 118 includes, prior to acquiring offset or dark images, synchronizing the offset scans with the one or more low frequency EMI signals (block 119). The method 118 includes acquiring one or more offset or dark images (i.e., detector data collected in the absence of radiation) (block 120). As described in greater detail below, the offset images may be utilized in determining a respective frequency of one or more low frequency EMI signals. The method 118 also includes synchronizing scans (e.g., scrubs and/or readouts) with the one or more EMI signals (block 122) once the X-ray image acquisition begins. The method 118 further includes starting the X-ray exposure (block 124). Subsequent to the beginning of the X-ray exposure, the method 118 includes acquiring X-ray image data, via the detector 22, during a synchronized image acquisition sequence (block 126). The method 118 further includes correcting the X-ray image data with the one or more acquired offset images to generate reconstructed images corrected for EMI artifacts. For example, each pixel of the image data may have the respective offset data for that pixel subtracted from it. In certain embodiments, the offset data utilized for correction may be from a single scan or an average of multiple scans (e.g., 4 offset scans). The synchronization of the image acquisition sequence enables the time dependent noise to be canceled out, thus, minimizing the row correlated noise.

Figure 7:
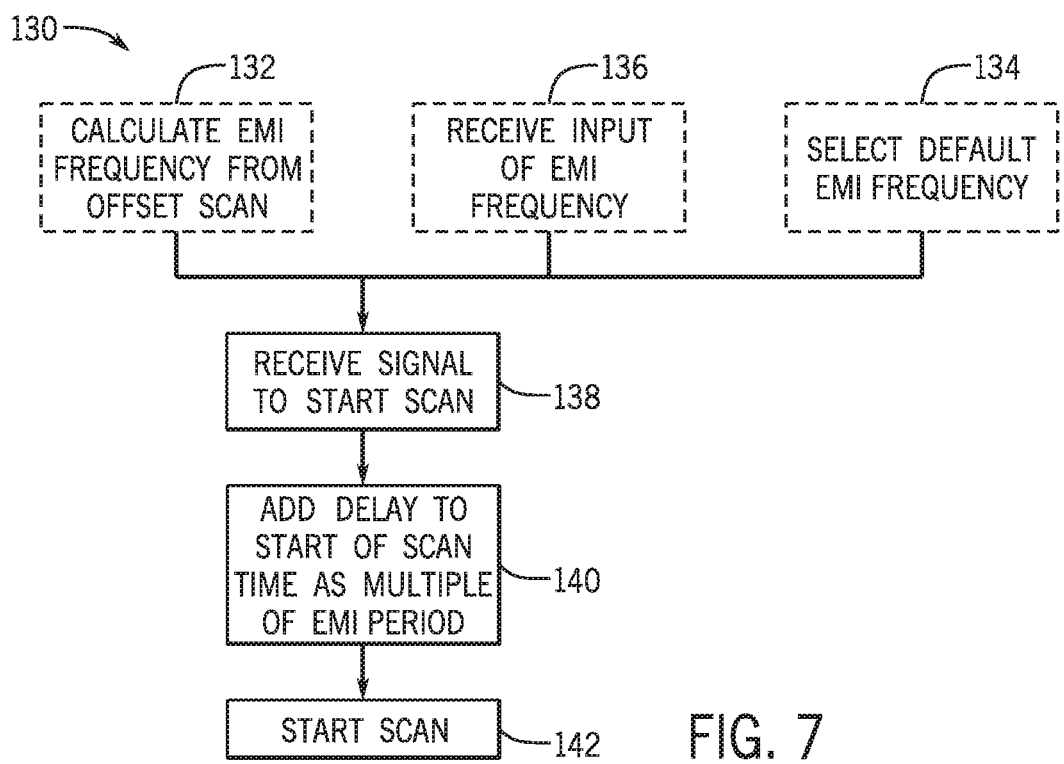
FIG. 7 is a flow chart of an embodiment of a method for synchronizing an image acquisition sequence.

FIG. 7 is a flow chart of an embodiment of a method 130 for synchronizing an image acquisition sequence (e.g., block 122 of the method 118). The method 130 may be performed by control/processing circuitry of the digital X-ray detector 22. In certain embodiments, the method 130 includes calculating an EMI frequency from offset data acquired prior to the X-ray exposure (block 132). In certain embodiments, more than one EMI frequency may be calculated in the presence of multiple low frequency EMI signals. Calculating the EMI frequency enables the detector 22 to perform auto-detection to determine the presence of low frequency EMI signals (e.g., 60 Hz or lower). Since the typical read time for a scan ranges from 100 to 300 milliseconds (ms), the low frequency EMI signals may be extracted via image analysis techniques (such as fast Fourier transformation (FFT) as described below). In certain embodiments, in the absence of an auto-detection, the frequency utilized for synchronization may default to a typical power line frequency (e.g., 50 Hz, 60 Hz, or a combination) while ignoring other low frequency EMI sources not linked to power lines (block 134). In certain embodiments, the method 130 includes receiving an input (e.g., user input) of the EMI frequency (block 136).

The method 130 includes receiving a signal (e.g., from control circuit 24 or system controller 28) to start the scan (e.g., readout or scrub) (block 138). The method 130 also includes adding a delay to the start of a scan time (e.g., the TBF or synchronization period), which is a multiple of the period of the EMI signal (block 140). For example, a 50 Hz EMI field has a period of 20 ms and a 60 Hz EMI field has a period of 16.666 ms. The TBF or synchronization period may be a multiple of 2, 3, 4, 5, or any other multiple of the period of the EMI signal. For example, the TBF or synchronization period may be 40 ms, 60 ms, 80 ms, 100 ms, or another period when associated with the 50 Hz EMI field. The TBF or synchronization period may be 33.333 ms, 49.999 ms, 66.666 ms, 83.333 ms, or another period when associated with the 60 Hz EMI field. In certain embodiments, the scans may be synchronized to multiple EMI frequencies (e.g., both 50 Hz and 60 Hz) at the same time. For example, the TBF or synchronization period to cancel out the 50 Hz and 60 Hz fields may be a multiple of the period of both frequencies such as 100 ms period (which is a multiple of 5 relative the period the 50 Hz field and a multiple of 6 to the 60 HZ field). The method 130 further includes starting the scan (e.g., readout) after the synchronization period (block 142).

Figure 8:
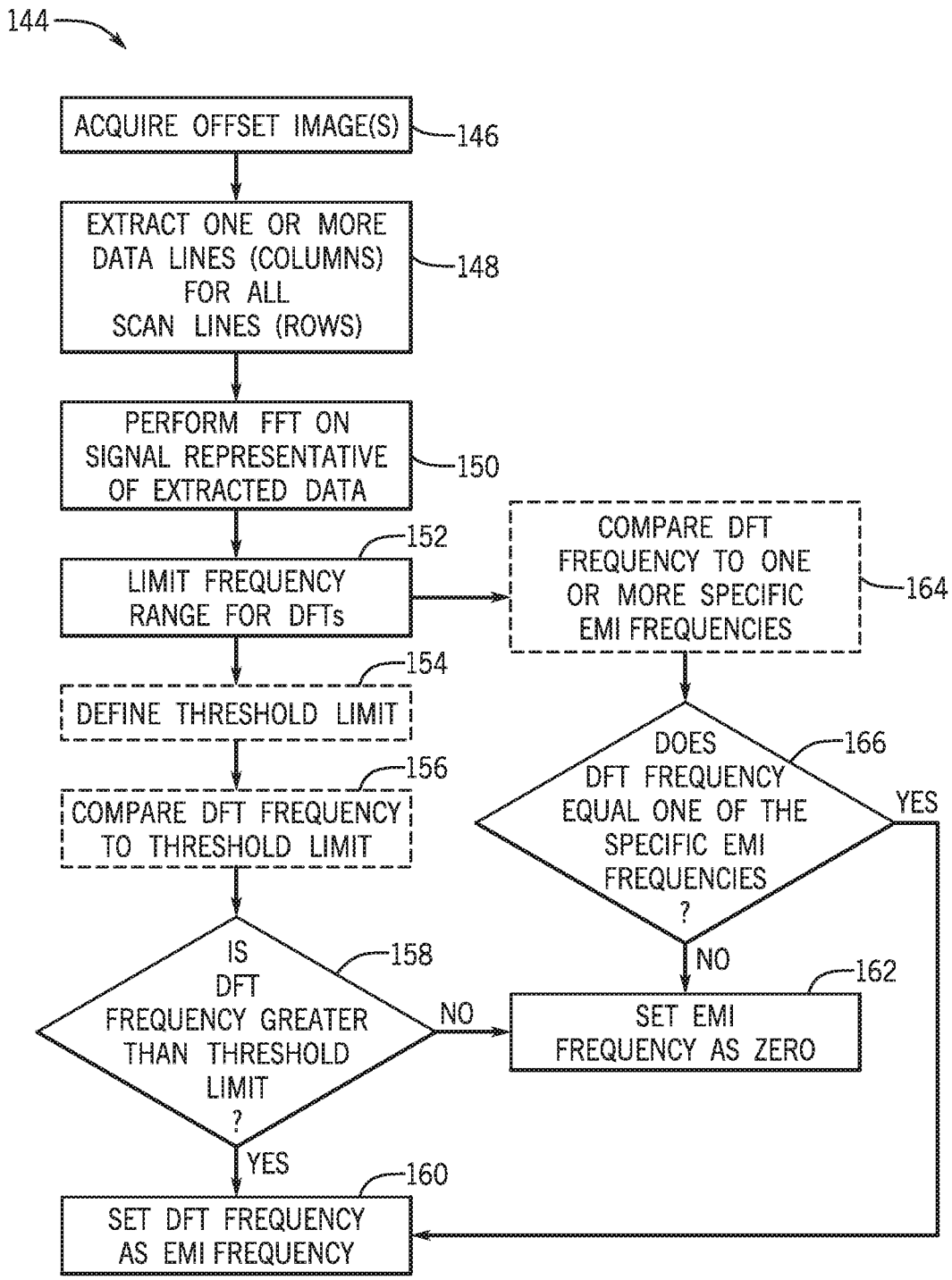
FIG. 8 is a flow chart of an embodiment of a method for determining a frequency of an EMI signal.

FIG. 8 is a flow chart of an embodiment of a method 144 for determining a frequency of an EMI signal or field (e.g., block 132 of the method 130). The method 144 may be performed by control/processing circuitry of the digital X-ray detector 22. It should be noted that the method 144 is a single example of an image analysis technique that may be utilized to extract the low frequency field from the offset image data. In addition, the method 144 may be utilized to determine the frequencies of multiple EMI signals or fields that are present. The method 144 includes acquiring one or more offset or dark images (i.e., detector data collected in the absence of radiation) (block 146). The method 144 also includes extracting a one or more data lines (from one or more columns) for all scans lines (i.e., rows) from a single offset scan or an average of multiple offset scans (block 148). The method 144 further includes performing FFT on a signal representative of the extracted data to generate a discrete Fourier transforms (DFTs) at different frequencies (block 150). The method 144 includes limiting the frequency of the DFTs to within a low frequency range defined by a lower frequency (f1) and a higher frequency (f2) so that frequency of the DFT is between f1 and f2 (block 152). In certain embodiments, the low frequency range may be defined by the frequency of a power line (e.g., 50 Hz, 60 Hz, etc.). The low frequency range may be plus or minus a percentage of the power line frequency (e.g., ±2 percent, ±3 percent etc.). For example, plus or minus 3 percent of 50 Hz would set f1 as 48.5 Hz and f2 as 51.5 Hz and plus or minus 3 percent of 60 Hz would set f1 as 58.2 Hz and f2 as 61.8 Hz.

In certain embodiments, the method 144 includes defining a threshold limit for comparison to the DFT frequency (block 154). In certain embodiments, the threshold limit may be determined experimentally. The method 144 may include comparing the DFT frequency to the threshold limit (block 156) to determine if the DFT frequency is greater than the threshold limit (block 158). If the DFT frequency is greater than the threshold limit, then the method 144 includes setting the DFT frequency as the EMI frequency (block 160). If the DFT frequency is not greater than the threshold limit, then the method 144 includes setting the EMI frequency as zero or null (block 162) and, thus, determining there is no EMI field.

In certain embodiments, after limiting the frequency range for the DFTs (block 152, the method 144 includes comparing the DFT frequency to one or more specific EMI frequencies (e.g., 50 Hz, 60 Hz, etc.) (block 164) to determine if the DFT frequency equals one of the specific EMI frequencies (block 166). If the DFT frequency equals a specific EMI frequency, the method 144 includes setting the DFT frequency as the EMI frequency (block 160). If the DFT frequency does not equal a specific EMI frequency, the method includes setting the EMI frequency as zero or null (block 162) and, thus, determining there is no EMI field.

Figure 9:
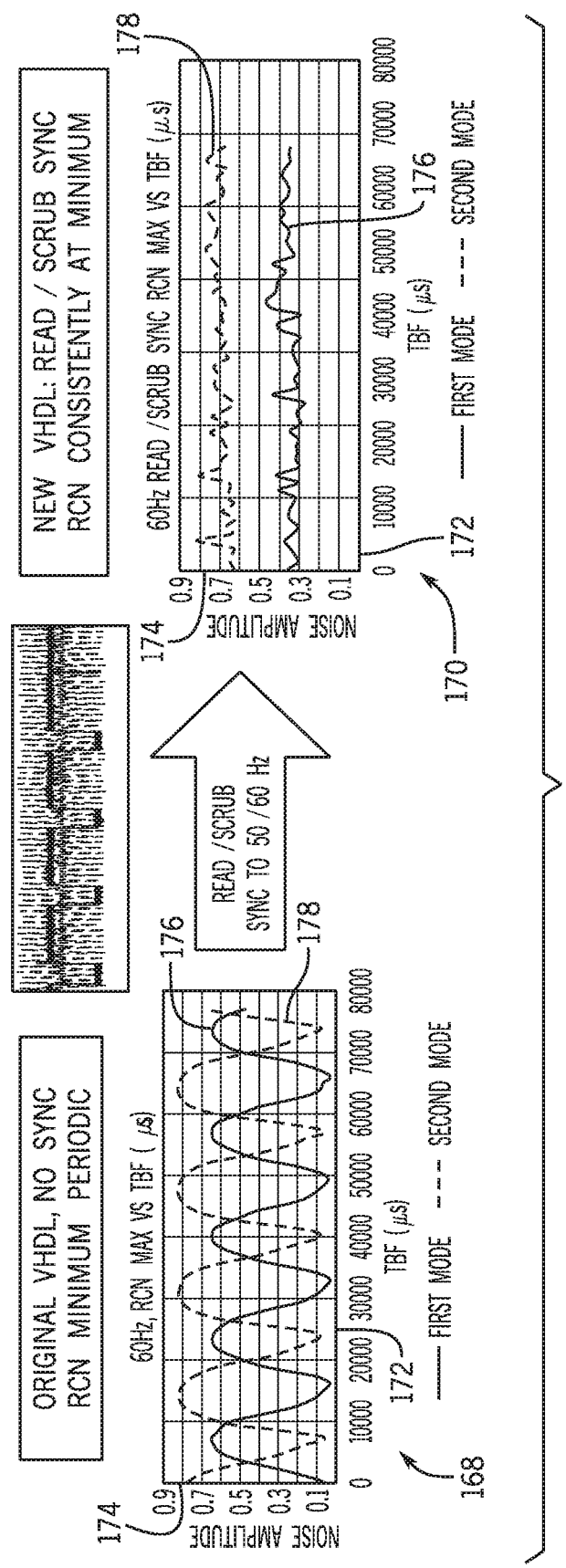
FIG. 9 is a schematic diagram illustrating the effect of synchronization of image acquisition to an EMI signal on row correlated noise.

FIG. 9 is a schematic diagram illustrating the effect of synchronization of image acquisition to an EMI signal on row correlated noise. FIG. 9 depicts two graph 168, 170. Each graph 168, 170 includes an X-axis 172 representing TBF in microseconds and a Y-axis 174 representing noise amplitude. The EMI signal is 60 Hz. Row correlated noise signal plots for two different imaging modes in response to the 60 HZ EMI signal are represented by plots 176 (solid), 178 (dashed), respectively. Graph 168 illustrates the row correlated noise relative to the TBF in the absence of synchronization of the scan (e.g., readout or scrub) to the period of the EMI signal. As depicted in graph 168, the row correlated noise varies with the TBF. In addition, as depicted in graph 168, the row correlated noise minimum is periodic. Graph 170 illustrates the row correlated noise relative to the TBF after synchronization of the scan to the period of the EMI signal. As depicted in graph 170, the row correlated noise is consistently at a minimum.

Technical effects of the disclosed embodiments include providing methods and systems to synchronize X-ray image acquisition sequences for radiographic detectors to minimize time dependent noise (e.g., row correlated noise) due to low frequency EMI (e.g., 60 Hz or less). The techniques discussed below may synchronize the scans (e.g., readout or scrub) of the detector to occur at a particular time period that is a multiple of a period of the EMI signal. In certain embodiments, the EMI frequency may be determined from offset data or dark images. The offset data may be utilized to correct the X-ray image data to generate corrected X-ray images where EMI artifacts are minimized due to the cancellation of the time dependent noise. The EMI mitigation techniques may be utilized across all orientations (X-, Y-, and Z-axes). The disclosed techniques may improve image quality in the presence of an EMI field as well as provide low frequency EMI immunity.

This written description uses examples to disclose the present subject matter, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A digital X-ray detector, comprising:
   control circuitry configured to:
      obtain an electromagnetic interference (EMI) frequency of an EMI signal;
      receive a signal to start a scan;

ensure EMI noise is in a same phase during acquisition of offset images and read images to enable a subtraction of the EMI noise; and
start the scan;
wherein the control circuitry is configured to obtain a respective EMI frequency of a plurality of EMI signals and to synchronize the scan based on the respective EMI frequencies so that a time of start for the scan is a multiple of each respective period of the plurality of EMI signals.

2. The digital X-ray detector of claim 1, wherein the scan comprises a scrub to reset detector circuitry or a read to acquire X-ray image data.

3. The digital X-ray detector of claim 1, wherein control circuitry is configured to obtain the EMI frequency via receiving a user input of the EMI frequency.

4. The digital X-ray detector of claim 1, wherein the control circuitry is configured to obtain the EMI frequency by calculating the EMI frequency from one or more offset scans acquired by the digital X-ray detector.

5. The digital X-ray detector of claim 4, wherein the control circuitry is configured to calculate the EMI frequency by extracting data from the one or more offset scans, performing fast Fourier transformation on a signal representative of the data, and determine if a frequency of a discrete Fourier transform (DFT) of the signal within a predetermined frequency range is greater than a defined frequency threshold.

6. The digital X-ray detector of claim 5, wherein the control circuitry is configured to set the EMI frequency as the frequency of the DFT when the frequency of the DFT is greater than the defined frequency threshold and to set the EMI frequency as zero when the frequency of the DFT is not greater than the defined frequency threshold.

7. The digital X-ray detector of claim 4, wherein the control circuitry is configured to calculate the EMI frequency by extracting data from the one or more offset scans, performing fast Fourier transformation on a signal representative of the data, and determine if a frequency of the discrete Fourier transform (DFT) of the signal equals a specific EMI frequency.

8. The digital X-ray detector of claim 7, wherein the control circuitry is configured to set the EMI frequency as the frequency of the DFT when the frequency of the DFT equals the specific EMI frequency and to set the EMI frequency as zero when the frequency of the DFT does not equal the specific EMI frequency.

9. An X-ray imaging method, comprising:
utilizing a digital X-ray detector to:
obtain an electromagnetic interference (EMI) frequency of an EMI signal, wherein obtaining the EMI frequency of the EMI signal comprises receiving a user input of the EMI frequency;
receive a signal to start a scan;
ensure EMI noise is in a same phase during acquisition of offset images and read images to enable a subtraction of the EMI noise; and
start the scan.

10. The method of claim 9, wherein the scan comprises a scrub to reset detector circuitry or a read to acquire X-ray image data.

11. The method of claim 9, wherein ensuring the EMI noise is in the same phase during acquisition of the offset images and the read images comprises synchronizing the scan based on the EMI frequency so that a time of start for the scan is a multiple of a period of the EMI signal.

12. The method of claim 9, wherein obtaining the EMI frequency of the EMI signal comprises calculating the EMI frequency from one or more offset scans acquired by the digital X-ray detector.

13. The method of claim 12, comprising:
acquiring, via the digital X-ray detector, X-ray image data with the scan; and
performing offset correction on the acquired X-ray image data with the one or more offset scans to remove any EMI related artifacts to generate a corrected X-ray image.

14. An imaging system comprising:
an X-ray source;
a digital X-ray detector; and
control circuitry configured, via the digital X-ray detector, to obtain an electromagnetic interference (EMI) frequency of an EMI signal, to receive a signal to start a scan, to ensure EMI noise is in a same phase during acquisition of offset images and read images to enable a subtraction of the EMI noise, and to start the scan;
wherein the control circuitry is configured, via the digital X-ray detector, to obtain a respective EMI frequency of a plurality of EMI signals and to synchronize the scan based on the respective EMI frequencies so that a time of start for the scan is a multiple of each respective period of the plurality of EMI signals.

15. The imaging system of claim 14, wherein the control circuitry is configured, via the digital X-ray detector, to obtain the EMI frequency by calculating the EMI frequency from one or more offset scans acquired by the digital X-ray detector.

16. The imaging system of claim 14, wherein the imaging system comprises processing circuitry, and the processing circuitry is configured to perform offset correction on acquired X-ray image data with the one or more offset scans to remove any EMI related artifacts to generate a corrected X-ray image.

* * * * *